(12) United States Patent
Sawai et al.

(10) Patent No.: US 6,391,851 B1
(45) Date of Patent: May 21, 2002

(54) HYDROCHLORIDES OF VANCOMYCIN ANTIBIOTICS AND PROCESS FOR PRODUCING THE SAME

(75) Inventors: Seiji Sawai, Takarazuka; Kenji Nishiwaki, Kobe; Kazumi Ohtomo, Ibaraki; Akira Kagayama, Ikoma, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/508,528

(22) PCT Filed: Sep. 11, 1998

(86) PCT No.: PCT/JP98/04098

§ 371 Date: Apr. 3, 2000

§ 102(e) Date: Apr. 3, 2000

(87) PCT Pub. No.: WO99/17793

PCT Pub. Date: Apr. 15, 1999

(30) Foreign Application Priority Data

Mar. 10, 1997 (JP) .............................. 9-270733

(51) Int. Cl.[7] .......................... A61K 38/16; C07K 9/00; C07G 11/00
(52) U.S. Cl. ................ 514/8; 514/9; 530/317; 530/322; 424/115; 424/118; 536/16.8; 536/16.9
(58) Field of Search ................ 514/8, 9; 430/317, 430/322; 424/115, 118; 536/16.8, 16.9

(56) References Cited

U.S. PATENT DOCUMENTS 4,885,275 A * 12/1989 Robinson ................ 514/8

FOREIGN PATENT DOCUMENTS

| EP | 0 318 146 | 10/1988 |
|---|---|---|
| EP | 0 438 747 A1 | 7/1991 |
| JP | 63010718 A | 1/1988 |

* cited by examiner

Primary Examiner—Christopher S. F. Low
Assistant Examiner—Abdel A. Mohamed
(74) Attorney, Agent, or Firm—McClelland, Maier & Neustadt, P.C.

(57) ABSTRACT

Process for producing a hydrochloride of a vancomycin antibiotic, comprising subjecting an aqueous solution of a hydrochloride of a vancomycin antibiotic to a primary freezing at from −1° C. to −20° C. for a time sufficient to grow ice crystals, to form a primarily frozen substance, then subjecting said primarily frozen substance to a secondary freezing at from −25° C. to −80° C. to form a completely frozen solid, and then drying the resulting frozen solid in vacuo; and product obtained by the process.

4 Claims, No Drawings

HYDROCHLORIDES OF VANCOMYCIN ANTIBIOTICS AND PROCESS FOR PRODUCING THE SAME

TECHNICAL FIELD

The present invention relates to hydrochlorides of vancomycin antibiotics and to process for producing the same.

BACKGROUND ART

Vancomycin antibiotics are amphoteric and strongly levorotatory glycopeptide antibiotics having relatively high molecular weight [Williams et. al., *Topics in Antibiotic Chemistry*, 5, 119–158 (1980)]. Examples of the known vancomycin antibiotics are vancomycin, ristocetin, actinoidin, teichomycin $A_2$, LL-AM-374, A477, OA7653 and A35512B. Vancomycin has been made into pharmaceutical preparations in a form of its hydrochloride for the therapy of infectious diseases, especially for the therapy of infectious diseases caused by Staphylococcus and by methicillin-resistant strains and has been supplied for oral and parenteral uses as a dried solid preparation filled in aseptic vials or small bottles. It is also useful as a substance for improving the utilizing rate of feed for ruminants.

For example, a dried solid of vancomycin hydrochloride is prepared by a freeze-drying of an aqueous solution of vancomycin hydrochloride but there is a disadvantage that, when the freeze-drying is finished, the said dried solid of vancomycin hydrochloride is hardly disintegrated and shows a poor filling property. In order to overcome such a disadvantage, a producing method which is characterized in conducting a freeze-drying prom a solution containing an organic solvent such as alcohol has been known (cf. U.S. Pat. No. 4,885,275) but there is a possibility that the organic solvent remains in the dried solid.

INDUSTRIAL APPLICABILITY

The present invention is to provide process for producing of hydrochlorides of vancomycin antibiotics which can be easily disintegrated and has excellent filling property from an aqueous solution of hydrochlorides of vancomycin antibiotics.

DISCLOSURE OF THE INVENTION

In accordance with the present invention, there is provided process for producing hydrochlorides of vancomycin antibiotics, characterized in that an aqueous solution of hydrochlorides of vancomycin antibiotics is subjected to a primary freezing at from −1° C. to −20° C. and then subjected to a secondary freezing at from −25° C. to −80° C., and the resulting frozen solid is dried in vacuo.

As hereunder, the process of the present invention is more specifically illustrated taking vancomycin hydrochloride as an example of hydrochlorides of vancomycin antibiotics.

Vancomycin is added to water (preferably water for injection) and is dissolved by adding hydrochloric acid (preferably 6N hydrochloric acid) with stirring and the solution is adjusted to pH 3.4–3.6 (preferably 3.45–3.50). Additional water (preferably water for injection) is added to prepare a vancomycin hydrochloride solution where the concentration of vancomycin is 10–20% (preferably 13–17%). Then this is subjected to an activated carbon treatment and/or filtration treatment through an aseptic filter if necessary and, after that, the said solution is filled in a container for freeze-drying (such as a tray made of stainless steel or vial, etc.; preferably a tray made of stainless steel).

Although thickness of the liquid is not particularly limited, the thickness of the liquid of 1–30 mm is preferred and the particularly preferred thickness of the liquid is 11–14 mm.

The vancomycin hydrochloride solution is subjected to a primary freezing at from −1 to −20° C. (preferably from −3° C. to −5° C.) as temperature of the container for freeze-drying until ice crystals grow in an entire solution. At that time, in order to make the formation of ice crystals easy, it is also possible that a quick cooling is firstly conducted down to about −20° C. to form ice crystals and then the primary freezing is carried out at the above-mentioned temperature. The resulting primarily frozen substance is subjected to a secondary freezing at from −25° C. to −80° C. (preferably from −35° C. to −45° C.) until it is completely frozen and solidified.

Drying of the resulting secondarily frozen substance may be carried out by means of drying in vacuo under warming in accordance with the conventional method for freeze-drying. Each of the above steps may be carried out under an aseptic condition if necessary.

Vancomycin which is used in the present invention is manufactured by multi-staged steps of purification and isolation from a fermentation broth prepared by fermentation of, for example, *Streptomyces orientalis* (cf. U.S. Pat. No. 3,067,099, etc.). Generally, the fermentation broth is filtered to remove solids and mycelia and purified using various kinds of adsorbent resin, etc., and the product is manufactured from the resulting concentrated solution by means of crystallization or freeze-drying. Purification may be carried out by a purifying method using a porous nonionic styrene-divinylbenzene copolymer as a resin (cf. U.S. Pat. No. 4,440,753); a purifying method using a peptide-immobilized ligand matrix (cf. U.S. Pat. No. 4,778,846 and U.S. Pat. No. 4,667,024); a purifying method where vancomycin is adsorbed with alumina and developed and eluted using an aqueous solution of hydrochloric acid containing an organic solvent such as methanol; a purifying method where vancomycin is adsorbed with an ion-exchange resin in which a carboxymethyl group is introduced into synthetic polymer gel having a hydrophilic hydroxyl group (such as a substance using polyvinyl gel as a synthetic polymer gel) and eluted with an aqueous solution of ammonium chloride, etc.; and the like. If necessary, two or more purifying methods may be combined.

BEST MODE FOR CARRYING OUT THE INVENTION

The present invention is described furthermore in detail by giving an example as hereunder although the said example does not limit the present invention.

EXAMPLE 1

(Two-step freeze-drying)

Vancomycin (450 g titer) was added to about 2.3 kg of water for injection and dissolved by stirring, the solution was adjusted to pH 3.45–3.50 by adding 6N hydrochloric acid thereto and then water for injection was added so as to make the total amount of 3.0 kg whereupon a vancomycin hydrochloride solution was prepared. The vancomycin hydrochloride solution prepared as such was dividedly placed in trays made of stainless steel to make the liquid thickness 11 mm and the trays were mounted in a freeze-drier.

The vancomycin hydrochloride solution was cooled to 5° C., and the trays were cooled down to −20° C. with 1 hour to form ice crystals and then raised up to 2° C. with 50 minutes. After that, the primary freezing was carried out at −3° C. as temperature of the trays for 13 hours, the said primarily frozen product was cooled to −40° C. as temperature of the trays with 1.5 hours and the secondary freezing was carried out at the same temperature for 2.5 hours. The resulting frozen solid was dried and solidified in vacuo at from 25° C. to 35° C. as temperature of the trays for 35.5 hours to give vancomycin hydrochloride (two-step freeze-dried product).

REFERENTIAL EXAMPLE 1

(One-step freeze-drying)

Trays which were prepared in the same manner as in Example 1 were mounted in a freeze-drier.

The vancomycin hydrochloride solution was cooled down to 5° C. then the trays were cooled down to −40° C. with 1.5 hours without conducting a primary freezing, and the secondary freezing was carried out at the same temperature for 2.5 hours. The resulting frozen solid was dried and solidified in vacuo at from 25° C. to 35° C. as temperature of the trays for 35.5 hours to give vancomycin hydrochloride (one-step freeze-dried product).

The two-step freeze-dried product prepared in the present invention is obtained as a powdery solid or a easily disintegratable solid and, therefore, in pouring into a hopper of a disintegrating machine, it is not necessary to carry out a rough disintegration which is required for a one-step freeze-dried product. In addition, the two-step freeze-dried product has an excellent filling property because it has less specific volume and less compressibility than the one-step freeze-dried product.

TEST EXAMPLE 1

Sieving Property

Test Method:

A test compound (100–200 g) was gently shaken for about one minute to pass a sieve having a nominal size of 2830 μm and the sieving property was evaluated by checking the amount of the tested substance remained on the sieve.

Test Results

TABLE 1

| Tested Substance | Effect |
| --- | --- |
| One-step freeze-dried product | About 30% (weight basis) remained on the sieve |
| Two-step freeze-dried product | All product passed through the sieve |

In the case of the two-step freeze-dried product, all of the product passed through the sieve and showed better sieving property than the one-step freeze-dried product which about 30% remained on the sieve.

From the above result, when a freeze-dried product is poured into the hopper of a disintegrating machine in an actual productional process, a roughly disintegrating process is necessary in the one-step freeze-dried product for preventing the retention in the hopper while, in the two-step freeze-dried product, a freeze-dried product which is already in a powdery state or is easily disintegrated is obtained and, accordingly, it is possible to eliminate the roughly disintegrating process.

TEST EXAMPLE 2

Filling Property

Test Method:

A test substance (about 100 g) was placed in a hopper of a machine for filling powder into vials (Ikeda Kikai Sangyo) and stirred for about one minute. A setting-up was done to make the filling amount about 0.5 g and a continuous filling into 100 vials was carried out. Filled amounts into the first ten vials and the last ten vials were calculated from the weight of vials before and after filling and the filling property was evaluated from the increasing rate of the filled amount.

Test Results

TABLE 2

| Test Substance | One-Step Freeze-Dried Product | Two-Step Freeze-Dried Product |
| --- | --- | --- |
| Filled Amount for First 10 Vials (average) | 0.526 g | 0.556 g |
| Filled Amount for Last 10 Vials (average) | 0.580 g | 0.580 g |
| Increasing Rate of Filling Amount | 10.0% | 6.3% |

It is apparent from the table that the two-step freeze-dried better showed less increasing rate of filled amount and better filling property than the one-step freeze-dried product.

What is claimed is:

1. Process for producing a hydrochloride of a vancomycin antibiotic, comprising subjecting an aqueous solution of a hydrochloride of a vancomycin antibiotic to a primary freezing at from −1° C. to −20° C. for a time sufficient to form ice crystals, to form a primarily frozen substance, then subjecting said primarily frozen substance to a secondary freezing at from −25° C. to −80° C. to form a completely frozen solid, and then drying the resulting frozen solid in vacuo.

2. The process according to claim 1, wherein the hydrochloride of the vancomycin antibiotic is vancomycin hydrochloride.

3. The process according to claim 1, wherein the primary freezing is carried out at from −2° C. to −5° C.

4. The process according to claim 3, wherein the secondary freezing is carried out at from −35° C. to −45° C.

* * * * *

UNITED STATES PATENT AND TRADEMARK OFFICE
CERTIFICATE OF CORRECTION

PATENT NO. : 6,391,851 B1
DATED : May 21, 2002
INVENTOR(S) : Sawai et al.

It is certified that error appears in the above-identified patent and that said Letters Patent is hereby corrected as shown below:

<u>Title page,</u>
Item [30], should read:

-- [30]     Foreign Application Priority Data
      Oct. 3, 1997    (JP) ………………………….. 9-270733 --

Signed and Sealed this

Fourth Day of February, 2003

JAMES E. ROGAN
*Director of the United States Patent and Trademark Office*